United States Patent
Ng et al.

(10) Patent No.: US 11,779,759 B2
(45) Date of Patent: Oct. 10, 2023

(54) STIMULATOR SYSTEMS AND METHODS FOR SELECTIVELY RECRUITING FASCICLES IN HYPOGLOSSAL NERVE TRUNK

(71) Applicant: THE ALFRED E. MANN FOUNDATION FOR SCIENTIFIC RESEARCH, Valencia, CA (US)

(72) Inventors: Boon Khai Ng, La Crescenta, CA (US); Joseph L. Calderon, Culver City, CA (US)

(73) Assignee: THE ALFRED E. MANN FOUNDATION FOR SCIENTIC RESEARCH, Valencia, CA (US)

( * ) Notice: Subject to any disclaimer, the term of this patent is extended or adjusted under 35 U.S.C. 154(b) by 191 days.

(21) Appl. No.: 17/190,612

(22) Filed: Mar. 3, 2021

(65) Prior Publication Data
US 2021/0187288 A1    Jun. 24, 2021

Related U.S. Application Data

(63) Continuation of application No. 16/118,348, filed on Aug. 30, 2018, now Pat. No. 10,967,178.
(Continued)

(51) Int. Cl.
*A61N 1/36* (2006.01)
*A61B 5/00* (2006.01)
(Continued)

(52) U.S. Cl.
CPC .......... *A61N 1/3601* (2013.01); *A61B 5/4818* (2013.01); *A61N 1/0556* (2013.01);
(Continued)

(58) Field of Classification Search
CPC ............................ A61N 1/3601; A61B 5/4818
(Continued)

(56) References Cited

U.S. PATENT DOCUMENTS 8,224,449 B2    7/2012   Carbunaru et al.
9,364,659 B1 *  6/2016   Rao .................... A61B 5/291
(Continued)

FOREIGN PATENT DOCUMENTS

WO   WO-2006135791 A2 * 12/2006   ........... A61N 1/0531
WO   WO2008092246        8/2008

OTHER PUBLICATIONS

PCT International Search Report and Written Opinion for International Appln. No. PCT/US2018/048978, Applicant The Alfred E. Mann Foundation for Scientific Research, forms PCT/ISA/210, 220, and 237, dated Nov. 22, 2018 (14 pages).

*Primary Examiner* — Nicole F Lavert
(74) *Attorney, Agent, or Firm* — Michael J. Bolan; VISTA IP LAW GROUP, LLP (57) ABSTRACT

An electrode lead comprises a lead body, connector contacts affixed to the proximal end of the lead body, and a cuff body affixed to the distal end of the lead body. The cuff body is pre-shaped to transition from an unfurled state to a furled state, wherein the cuff body, when in the furled state has an inner surface for contacting a nerve and an overlapping inner cuff region and an outer cuff region. The electrode lead further comprise electrode contacts circumferentially disposed along the cuff body when in the furled state, such that at least one of the electrode contacts is located on the inner surface of the cuff body, and at least another of the electrode contacts is located between the overlapping inner and outer cuff regions. The electrode lead further comprises electrical conductors extending through the lead body respectively between the connector contacts and the electrode contacts.

11 Claims, 10 Drawing Sheets

Related U.S. Application Data (60) Provisional application No. 62/552,266, filed on Aug. 30, 2017.

(51) Int. Cl.
*A61N 1/05* (2006.01)
*A61N 1/372* (2006.01)
*A61N 1/378* (2006.01)
*A61B 5/394* (2021.01)

(52) U.S. Cl.
CPC ...... *A61N 1/36139* (2013.01); *A61N 1/37211* (2013.01); *A61B 5/394* (2021.01); *A61B 5/4836* (2013.01); *A61B 2562/0219* (2013.01); *A61N 1/3611* (2013.01); *A61N 1/3787* (2013.01)

(58) Field of Classification Search
USPC .......................................................... 607/42
See application file for complete search history.

(56) References Cited

U.S. PATENT DOCUMENTS

| | | | |
|---|---|---|---|
| 2008/0132983 A1* | 6/2008 | Cohen | A61N 1/36114 607/118 |
| 2015/0073501 A1* | 3/2015 | Moffitt | A61N 1/0534 607/116 |
| 2015/0224307 A1* | 8/2015 | Bolea | A61N 1/3611 607/42 |
| 2015/0374975 A1* | 12/2015 | Callegari | A61N 1/0556 29/874 |

* cited by examiner

STIMULATOR SYSTEMS AND METHODS FOR SELECTIVELY RECRUITING FASCICLES IN HYPOGLOSSAL NERVE TRUNK

CROSS-REFERENCE TO RELATED APPLICATION(S)

The present application is a continuation of U.S. patent application Ser. No. 16/118,348, filed Aug. 30, 2018 (now U.S. Pat. No. 10,967,178), which claims the benefit of priority to U.S. Provisional Application Ser. No. 62/522,266, filed on Aug. 30, 2017. The contents of the aforementioned patent applications are hereby expressly incorporated by reference in their entirety.

FIELD OF THE INVENTION

The present invention relates to systems and methods for the treatment of obstructive sleep apnea (OSA), and more specifically for the treatment of OSA by stimulating the hypoglossal nerve (HGN) trunk.

BACKGROUND

Obstructive sleep apnea (OSA) is a highly prevalent sleep disorder that is caused by the collapse of or increase in the resistance of the pharyngeal airway, often resulting from tongue obstruction. The obstruction of the upper airway is mainly caused by reduced genioglossus muscle activity during the deeper states of NREM sleep. Obstruction of the upper airway causes breathing to pause during sleep. Cessation of breathing causes a decrease in the blood oxygen saturation level, which is eventually corrected when the person wakes up and resumes breathing. The long-term effects of OSA include high blood pressure, heart failure, strokes, diabetes, headaches, and general daytime sleepiness and memory loss, among other symptoms.

OSA is extremely common, having a similar prevalence as diabetes or asthma. Over 100 million people worldwide suffer from OSA, with about 25% of those being treated. Continuous Positive Airway Pressure (CPAP) is the usual established therapy for people who suffer from OSA. More than five million patients own a CPAP machine in North America, but many do not comply with use of these machines, because they cover the mouth and nose and, hence, are cumbersome and uncomfortable.

The use of neurostimulators to open the upper airway has been explored by several companies as a treatment for alleviating apneic events. Such therapy involves stimulating the nerve fascicles of the hypoglossal nerve (HGN) that innervate the intrinsic and extrinsic muscles of the tongue in a manner that prevents retraction of the tongue, which would otherwise close the upper airway during inspiration of the respiratory cycle.

ImThera Medical is currently in FDA clinical trials for a stimulator system that is used to stimulate the trunk of the HGN with a nerve cuff electrode. The stimulation system does not provide a sensor or sensing, and therefore, the stimulation delivered to the HGN trunk is not synchronized to the respiratory cycle. Thus, the tongue and other muscles that are innervated by nerve fascicles of the HGN trunk are stimulated irrespective of the respiratory cycle.

The rationale for this treatment method appears to be that it is enough simply to tone the tongue muscle and other nearby muscles, so that the tongue muscle does not retract in a manner that would cause obstructive sleep apnea. The belief is that it is not necessary to specifically target the protraction (i.e., anterior movement) of the tongue muscle and to synchronize the occurrence of tongue protraction when it is most needed, i.e., during inspiration. The nerve cuff electrode of the ImThera Medical system has multiple electrode contacts helically surrounding the proximal part of the HGN nerve trunk. So, instead, each electrode contact delivers stimulation in a sequential order to the HGN trunk. For example, if a three-electrode contact nerve cuff is used, electrode contact #1 stimulates, then stops, electrode contact #2 stimulates, then stops, electrode contact #3 stimulates, then stops, then electrode contact #1 stimulates, then stops and so on. Since all or most electrode contacts deliver stimulation, there is no selection process to choose the best one or two electrode contact or contacts that is finally used to deliver the best stimulation to alleviate sleep apnea.

However, because the HGN trunk contains nerve fascicles that innervate muscles other than the muscle that extend the tongue, the Imthera Medical method of stimulation at the HGN trunk does not just target the specific protrusor tongue muscles, but may stimulate other tongue muscles that are not targeted.

Another company, Inspire Medical Systems, Inc., does offer a stimulation system with a sensor, and therefore does attempt to time the onset of stimulation to the breathing cycle. This system, which is FDA approved for sale in the United States since April 2010, uses a simple, bipolar electrode (two electrode contacts only) within a nerve cuff electrode and implants the electrode at the branch of the HGN that is responsible for protruding the tongue. A simple, two-electrode contact cuff electrode can be used at the branch nerve, unlike the HGN trunk, because at the distal branch location, the nerve fascicles generally innervate the specific tongue protrusor muscle and not other muscles.

However, implanting the electrode at a branch of the HGN takes additional surgery time, which increases trauma to the patient and increases the substantial expense of operating room time. By attaching the nerve cuff electrode to the proximal section of the main trunk of the HGN, compared to placing the nerve cuff electrode at the more distal end of the HGN, it estimated that the surgical time will be reduced by approximately one hour. Even more importantly, because the branch nerve is small and more difficult to isolate than the HGN trunk, implanting a nerve cuff electrode at the branch site demands heightened expertise from the otolaryngologist/Ear Nose and Throat (ENT) surgeon or neurosurgeon, which significantly increases the chance for error and surgical risks. Furthermore, because the distal location of the HGN has a smaller diameter of nerves, and hence the required electrode contacts need to be smaller, the smaller nerve cuff electrode may be more difficult to manufacture.

Thus, it is desirable to implant the nerve cuff electrode at the trunk of the hypoglossal nerve. However, one must then deal with the fact that the target nerve fascicles are not easily isolated and stimulated, while at the same time avoiding stimulating other fascicles in the same nerve trunk.

There, thus, remains a need for improved systems and methods for selectively recruiting only specific fascicles of the hypoglossal nerve, while minimizing the surgery time and effort required to implant the neurostimulation components in the patient.

SUMMARY

In accordance with a first aspect of the present inventions, an electrode lead comprises an elongated lead body having a proximal end and a distal end, an array of connector contacts affixed to the proximal end of the lead body, and a biologically compatible, elastic, electrically insulative cuff body affixed to the distal end of the lead body. The electrode lead further comprises an array of electrode contacts (which may number at least three, and preferably at least six) circumferentially disposed along the cuff body when in the furled state, such that at least one of the electrode contacts is located on the inner surface of the cuff body, and at least another of the electrode contacts is located between the overlapping inner and outer cuff regions. The electrode lead further comprises a plurality of electrical conductors extending through the lead body respectively between the array of connector contacts and the array of electrode contacts.

The cuff body is pre-shaped to transition from an unfurled state to a furled state, wherein the cuff body, when in the furled state has an inner surface for contacting a nerve and an overlapping inner cuff region and an outer cuff region. The inner surface of the furled cuff body may have a diameter in the range of 2.5 mm to 4.0 mm. In one embodiment, only one of the electrode contacts is located between the overlapping inner and outer cuff regions. In another embodiment, when the cuff body is in the unfurled state, a center-to-center spacing of each pair of adjacent ones of electrode contacts is equal to or less than twice a width of each electrode contact of the respective pair of electrode contacts.

In accordance with a second aspect of the present inventions, a neurostimulation system comprises the afore-described electrode lead, and a neurostimulator comprising a connector configured for receiving the proximal contacts of the electrode lead, and stimulation circuitry configured for generating and delivering an electrical stimulation pulse train to at least one of the electrode contacts of the electrode lead.

In accordance with a third aspect of the present inventions, a method of using the afore-described electrode lead comprises maintaining the cuff body in the unfurled state while placing the cuff body in contact with the nerve (which may be, e.g., a trunk of a hypoglossal nerve (HGN)), and placing the cuff body from the unfurled state into the furled state, such that the cuff body wraps around the nerve. In one method, the size of the nerve allows the cuff body to wrap upon itself, such that the one electrode contact(s) are in contact with the nerve, and the other electrode contact(s) are between the overlapping inner and outer cuff regions without contacting the nerve. In another method, the size of the nerve may prevent the cuff body from wrapping upon itself, such that all of the electrode contacts are in contact with the nerve. When the cuff body is wrapped around the nerve, a center-to-center spacing of each pair of adjacent ones of electrode contacts is equal to or less than twice a width of each electrode contact of the respective pair of electrode contacts. Still another method further comprises delivering electrical stimulation energy to one or more of the electrode contacts to stimulate the nerve. For example, the electrical stimulation energy may be delivered between a pair of adjacent ones of the electrode contacts to stimulate the nerve in a bipolar mode.

In accordance with a fourth aspect of the present inventions, a method of implanting an electrode lead in a patient is provided. The electrode lead comprises a biologically compatible, elastic, electrically insulative cuff body and an array of electrode contacts (which may number at least three, and preferably at least six) disposed along the cuff body. The method comprises wrapping the cuff body upon itself around a nerve (which may be, e.g., a trunk of a hypoglossal nerve (HGN) and may be in the range of 2.5 mm to 4.0 mm) of the patient, such that there exists an inner surface that contacts the nerve and an overlapping inner cuff region and an outer cuff region, at least one of the electrode contacts being on the inner surface in contact with the nerve, and at least another of the electrode contacts being between the inner and outer overlapping regions of the cuff body without contacting the nerve. In one method, only one of the electrode contacts is located between the overlapping inner and outer cuff regions.

The cuff body may be pre-shaped to transition from an unfurled state to a furled state, in which case, the method may further comprise maintaining the cuff body in the unfurled state while placing the cuff body in contact with the nerve, and placing the cuff body from the unfurled state into the furled state, such that the cuff body wraps upon itself around the nerve. The cuff body may be wrapped around itself around the nerve, in which case, a center-to-center spacing of each pair of adjacent ones of electrode contacts is equal to or less than twice a width of each electrode contact of the respective pair of electrode contacts.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION

It is believed that obstruction to the upper airways is primarily caused by reduced genioglossus muscle activity during the deeper stages of NREM sleep. The present invention provides a system and method for moving the glossus (tongue) anteriorly using electrical stimulation to prevent the obstruction of the airway during sleep.

Figure 1:
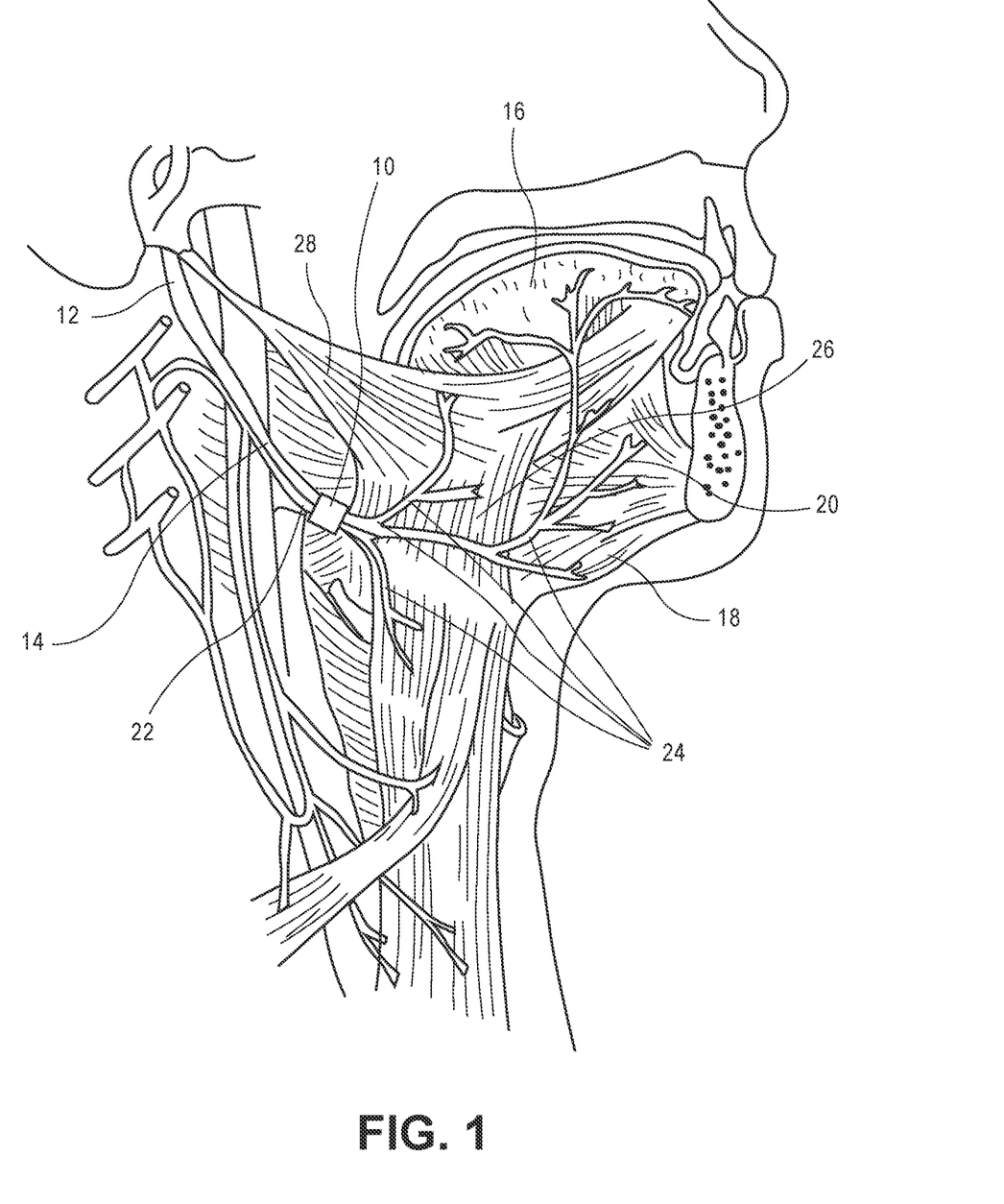
FIG. 1 is a cut-away anatomical drawing of the head and neck area illustrating the muscles that control movement of the tongue and the hypoglossal nerve and its branches that innervate these muscles.

Referring first to FIG. 1, it is desirable to locate a nerve cuff electrode 10 around a trunk 14 of a hypoglossal nerve (HGN) 12 for purposes of stimulating the muscles that anteriorly move the tongue 16, and in particular, the fascicles of the HGN 12 that innervate the tongue protrusor muscles, such as the genioglossus 18 and/or the geniohyoid muscles 20. As shown, the nerve cuff electrode 10 is positioned on the HGN trunk 14 immediately before it branches out, and hence at a proximal position 22 to the HGN branches 24. As briefly discussed above, the implantation of the nerve cuff electrode 10 at this proximal position 22 reduces the surgical time and effort, allows more surgeons to perform the surgery, reduces the risk and trauma to the patient, and reduces engineering design complexity and cost. However, it introduces the problem of inadvertently stimulating other fascicles of the HGN trunk 14 that innervate muscles in opposition to the genioglossus 18 and/or the geniohyoid muscles 20, i.e., the tongue retractor muscles, e.g., the hyoglossus 26 and styloglossus muscles 28, as well as the intrinsic muscles of the tongue 16.

Figure 2:
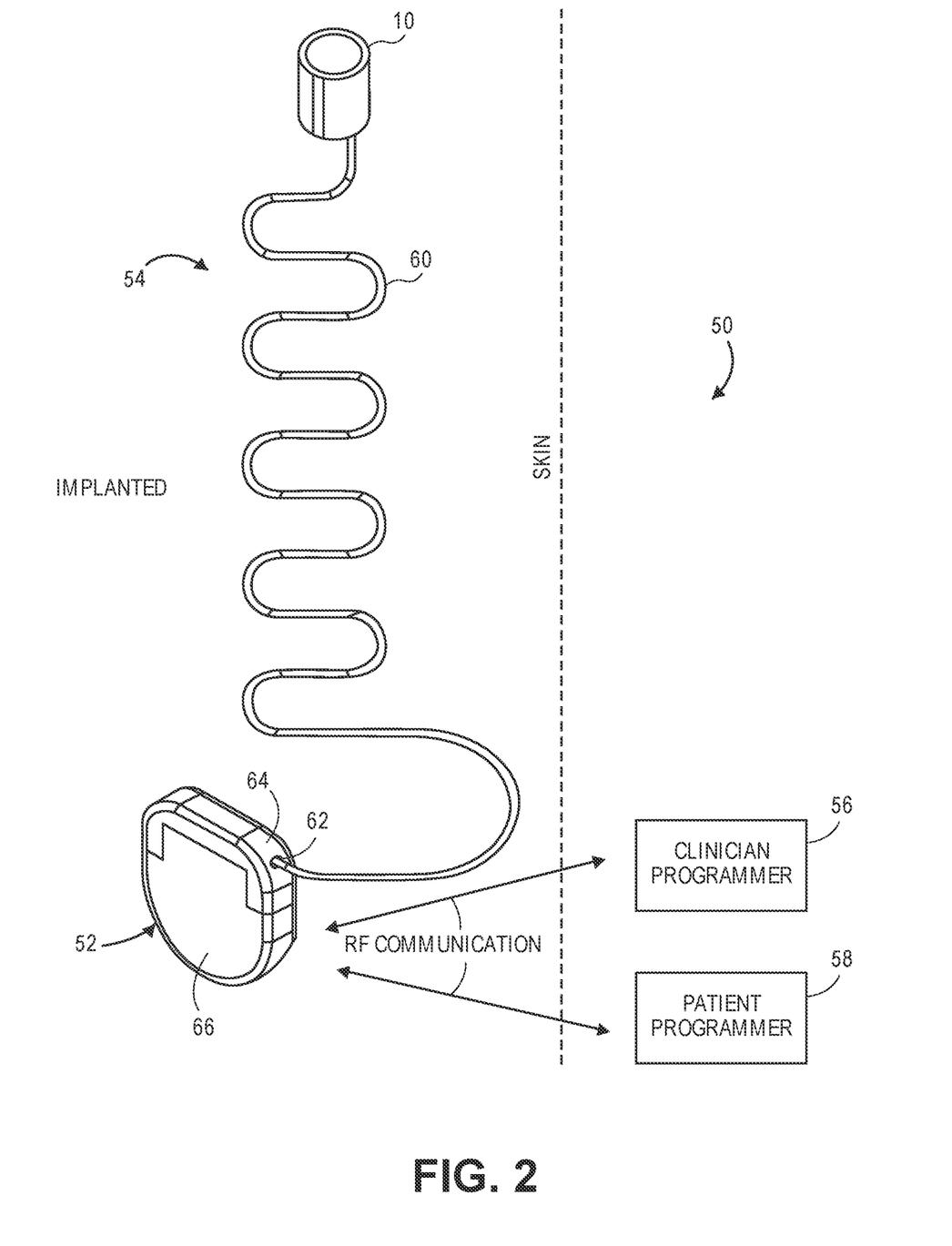
FIG. 2 is a plan view of a stimulation system constructed in accordance with one embodiment of the present inventions.

Referring to FIG. 2, one embodiment of a stimulation system 50 that selectively stimulates the fascicles of the trunk 14 of the HGN 12 that innervate the genioglossus 18 and/or the geniohyoid 20 muscles for treating obstructive sleep apnea will now be described. The system 50 generally comprises an implantable device 52, an electrode lead 54, a clinician programmer 56, and a patient programmer 58. The implantable device 52, or alternatively, an implantable pulse generator ("IPG") or equivalently a "stimulator" can be implanted within a patient.

The electrode lead 54 comprises the aforementioned nerve cuff electrode 10, a lead body 60 coupling the nerve cuff electrode 10 to the implantable device 52 via a proximal lead connector 62 and a corresponding connector receptacle 64. Although the lead body 60 can be straight, in the illustrated embodiment, the lead body 60 may have one or more S-shaped sections in order to provide strain relief in order to accommodate body movement at the location where the lead body 60 is implanted. This strain relief feature is advantageous, since the lead body 60 is intended to be implanted in a body location such as the neck, where the lead body 60 is subjected to frequent movement and stretching. Thus, the S-shape of the lead body 60 can help prevent damage to the HGN trunk 14, resulting from sometimes, unavoidable pulling of the nerve cuff electrode 10 as a result of neck movements. As will be described in further detail, the nerve cuff electrode 10 comprises an array of circumferentially disposed electrode contacts.

Although only a single electrode lead 54 is shown in FIG. 2, some embodiments of the present system may have an IPG 52 having two receptacles 64 (not shown) for attaching two electrode leads, each electrode lead having a nerve cuff electrode 10. In such a two-electrode lead system, each nerve cuff electrode 10 can be implanted bilaterally to each of the HGN trunks 14. However, it has been determined that only a single nerve cuff electrode 10 implanted at the HGN trunk 14 on either side (unilaterally) can provide sufficiently effective stimulation to protrude the tongue to control obstructive sleep apnea. A unilateral stimulation system is advantageous, since it is simpler in numbers of components used and requires only half the surgery to implant only a single nerve cuff electrode 10, instead of two.

The IPG 52 comprises an outer case 66 for housing the electronic and other components (described in further detail below). In one embodiment, the outer case 66 is composed of an electrically conductive, biocompatible material, such as titanium, and forms a hermetically sealed compartment wherein the internal electronics are protected from the body tissue and fluids. In some cases, the outer case 66 may serve as an electrode. As briefly discussed above, the IPG 52 further comprises a receptacle 64 to which the proximal end of the lead body 60 mates in a manner that electrically couples the nerve cuff electrode 10 to the internal electronics (described in further detail below) within the outer case 66.

Figure 3:
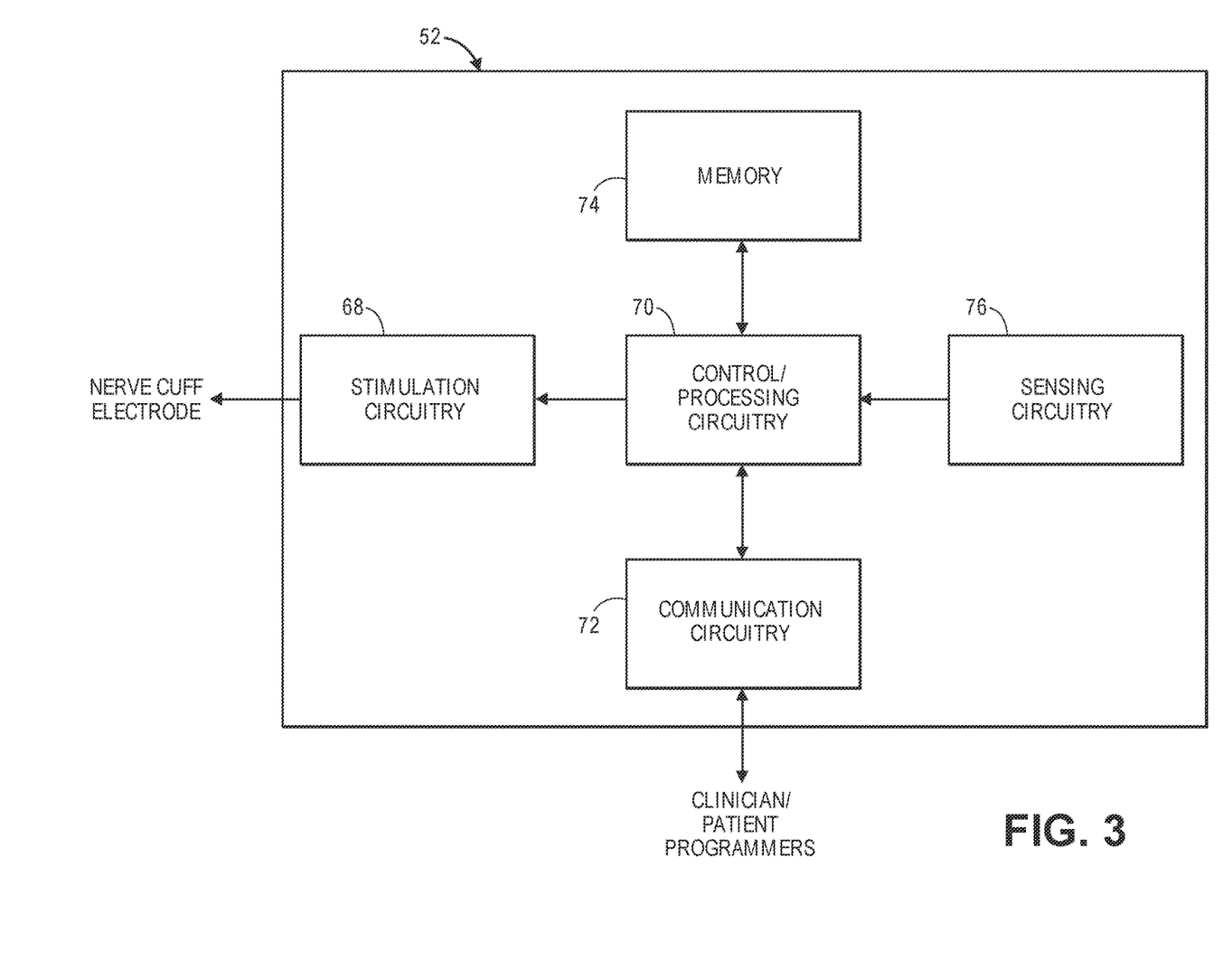
FIG. 3 is a block diagram of the internal components of an implantable pulse generator of the stimulation system of FIG. 2.

Referring further to FIG. 3, the components and circuitry housed in the outer case 66 may comprise stimulation circuitry 68, control circuitry 70, communication circuitry 72, memory 74, and sensing circuitry 76. The stimulation circuitry 68, control circuitry 70, communication circuitry 72, memory 74, and sensing circuitry 76 may be conveniently mounted on a printed circuit board (PCB) (not shown).

In one embodiment, the sensing circuitry 76 comprises one or more sensor(s) (not shown) that are contained in the outer case 66, although in alternative embodiments, the sensor(s) may be affixed to the exterior of the outer case 66. In other alternative embodiments, the sensor(s) can be positioned at a site remote from the IPG 52 coupled by a connecting lead, e.g., as described in U.S. Patent Publication No. 2016/0354608), entitled "Upper Airway Stimulator Systems for Obstructive Sleep Apnea," which is expressly incorporated herein by reference in its entirety.

The sensing circuitry 76 can detect physiological artifacts that are caused by respiration (e.g., motion or ribcage movement), which are proxies for respiratory phases, such as inspiration and expiration or, if no movement occurs, to indicate when breathing stops. For example, the sensing circuitry 76 may sense movement of the thoracic cavity and/or detect changes in pressure/force in the thoracic cavity. Thus, the sensing circuitry 76 is configured for acquiring, conditioning, and processing signals related to respiration. The sensor(s) of the sensing circuitry 76 can take the form of, e.g., inertial sensors (e.g., accelerometers), bioimpedance sensors, pressure sensors, gyroscopes, ECG electrodes, temperature sensors, GPS sensors, or some combination thereof.

The stimulation circuitry 68 is coupled to the nerve cuff electrode 10 via the lead body 60, and is configured for delivering stimulation to the HGN trunk 14. The control circuitry 70 is coupled to the stimulation circuitry 68 and controls when, and for how long, the stimulation circuitry 68 applies stimulation to the HGN trunk 14. The control circuitry 70 may also control the intensity of the stimulation applied by the stimulation circuitry 68 to the HGN trunk 14, e.g., by varying the amplitude, pulse width, or frequency of the stimulation. The control circuitry 70 may select the optimal electrode contact(s) of the nerve cuff electrode 10 used for stimulating the HGN trunk 14, and in particular, the electrode contacts that stimulate the fascicles of the HGN 14 innervating the genioglossus 18 or geniohyoid 20 protrusor muscles over the fascicles innervating the tongue retractor muscles, e.g., the hyoglossus 26 and styloglossus muscles 28, as well as the intrinsic muscles of the tongue 16, thereby preventing or alleviating obstructive apneic events.

The memory 74 is configured for storing specific data gathered by the sensing circuitry 76 and programming instructions and stimulation parameters. The control circuitry 70 may recall the sensed data from the memory 74 and analyze it to determine when stimulation should be delivered to synchronize the stimulation delivery with the respiratory cycle. In some embodiments, the sensor data may be analyzed to predict the onset of the next inspiratory phase of the breathing cycle and to deliver stimulation right before, at, or slightly after the predicted onset of the inspiratory phase.

Thus, when the patient is in the inspiratory portion of the respiratory cycle—where the patient is breathing in or attempting to breath in, the control circuitry 70 may condition the application of stimulation upon the patient being in this inspiratory phase of respiration, thereby causing anterior displacement of the tongue, and causing the upper airway to remain un-obstructed during inspiration while sleeping. The control circuitry 70 causes the stimulation circuitry 68 to apply stimulation in the form of a train of stimulation pulses during these inspiratory phases of the respiratory cycle (or applying stimulation starting slightly before the inspiration and ending at the end of inspiration), and not the remainder of the respiration cycle, when all other conditions for stimulation are met. The train of stimulus pulses may be set to a constant time duration or it may be adaptive, meaning that duration of the train of pulses can change dynamically based on a predictive algorithm that determines the duration of the inspiratory phase of the respiratory cycle. The communication circuitry 72 is configured for wirelessly communicating transcutaneously (through the patient's skin) with the clinician programmer 56 and patient programmer 58 using radio frequency (RF) signals, e.g., via an Off The Shelf (OTS) inductive/Bluetooth/MICS radio link.

The clinician programmer 56 may be used to program the IPG 52 and query the IPG 52 for status. For example, the clinician programmer 56 can be used to configure certain programs and processes used by the control circuitry 70 in the IPG 52 to determine when the stimulation pulses are to be delivered to electrode contacts of the nerve cuff electrode 10. The clinician programmer 56 can also be used to program specific stimulus parameters, such as stimulus pulse width, stimulus frequency, duration of a train pulses and pulse amplitude. The amplitude may be expressed in current, for example, milliamperes, or it could be expressed in volts, such as 0.3 volts. The choice between milliamperes or volts to express stimulus amplitude will depend on whether the design of the stimulation circuitry 68 provides stimulus pulses that are constant voltage or constant current. Another important function of the clinician programmer 56 is the ability to select modes of stimulation. For example, the IPG 52 may operate in a monopolar stimulation mode (also sometimes referred to as a "unipolar" mode) and in a bipolar stimulation mode.

As used in this present disclosure, a monopolar stimulation mode means that one of the electrode contacts used is at least a portion of the outer case 66 that will function as an indifferent/anode electrode. The indifferent electrode is part of the electrical circuit with at least one electrode contact of the nerve cuff electrode 10 as the active/cathode electrode contact that stimulates the HGN trunk 14. Generally, that part of the outer case 66 that is acting as the indifferent electrode does not stimulate any tissue or nerve, but merely functions as a return electrode and may be a biocompatible, conductive metal such as a titanium alloy, as discussed above.

A bipolar stimulation mode means, for purposes of this disclosure, that the outer case 66 is not part of the stimulation circuit. At least two electrode contacts of the nerve cuff electrode 10 must be selected and will be part of the bipolar mode electrical stimulation circuit. Sometimes a stimulation circuit can have three or even more electrode contacts functioning together. This may also be referred to as "bipolar" stimulation mode even though there are sometimes more than two active electrode contacts in the stimulation circuit. Sometimes a three-electrode contact system may be referred to as a tripolar circuit. For purposes of this disclosure and application, we will consider a three or more electrode-contact stimulation circuit (if it excludes the outer case 66) as variants of a bipolar stimulation mode and will be included as within a "bipolar" stimulation mode. The present stimulation system in its various embodiments, thus, may operate in either monopolar or bipolar stimulation modes.

In addition to choosing stimulation modes, the clinician programmer 56 also can choose which electrode contacts of the nerve cuff electrode 10 or the indifferent electrode of the outer case 66 are to be in the stimulation circuit. It may be possible, for example, to have three electrode contacts active simultaneously, where a middle electrode contact is delivering a cathodic phase of stimulus pulse, while the two surrounding electrode contacts are anodes in the anodic phase of the stimulus. The clinician programmer 56 may also be able to query the status of the IPG 52 for a number of status functions, such as battery status. Another query may be whether the IPG 52 is in an ON mode or an OFF mode. In the ON mode, the stimulation circuitry 68 within the IPG 52 is enabled and stimulation pulses can be delivered via the selected electrode contact or contacts of the nerve cuff electrode 10. When the patient is awake, the IPG may be placed automatically or by choice into the OFF position or mode, and the stimulation circuitry 68 is not enabled and no stimulation can occur.

The patient programmer 58 offers more limited programming options than the clinician programmer 56. The patient programmer 58 may provide the option to toggle the IPG 52 into the OFF mode or into the ON mode. Also, the stimulus pulse amplitudes may be adjusted for a limited range of up and down. Often the patient programmer 58, because of limited functionality, may be in a package or form that is much smaller in size than the clinician programmer 56. The clinician programmer 56 and patient programmer 58 may take the form of commercial electronic smart devices on which there are installed customized applications for performing the afore-described functions.

In an optional embodiment, the IPG 52 may have a magnetic reed switch (not shown) contained within the outer case 66 that can sense a magnetic field from an external magnet. An external magnet may be used to toggle the IPG 52 to the OFF position or alternatively to an ON position. Often, patients may need to undergo an MRI scan. A reed switch in the IPG 52 may make it MRI incompatible. In another embodiment, the IPG may contain a sensor (not shown) that is sensitive to movement, such as an inertial sensor or an accelerometer, and can be toggled between an ON position and an OFF position by tapping the implanted IPG 52, for example, with the hand; for example, one tap to switch the IPG 52 from an ON position to an OFF position, and one tap to switch the IPG 52 from an OFF position to an ON position. In a particularly preferred embodiment, the IPG 52 can be toggled between an ON position and an OFF position in response to multiple quick successive taps, as opposed to a single tap, which may occur by accidental bumping and cause an inadvertent turn off of the IPG; for example, two taps to switch the IPG 52 from an ON position to an OFF position, and two taps to switch the IPG 52 from an OFF position to an ON position. As a redundancy, the patient programmer 58 or the clinician programmer 56 may also be configured to be able to toggle the IPG 52 from ON to OFF and from OFF to ON.

Figure 4:
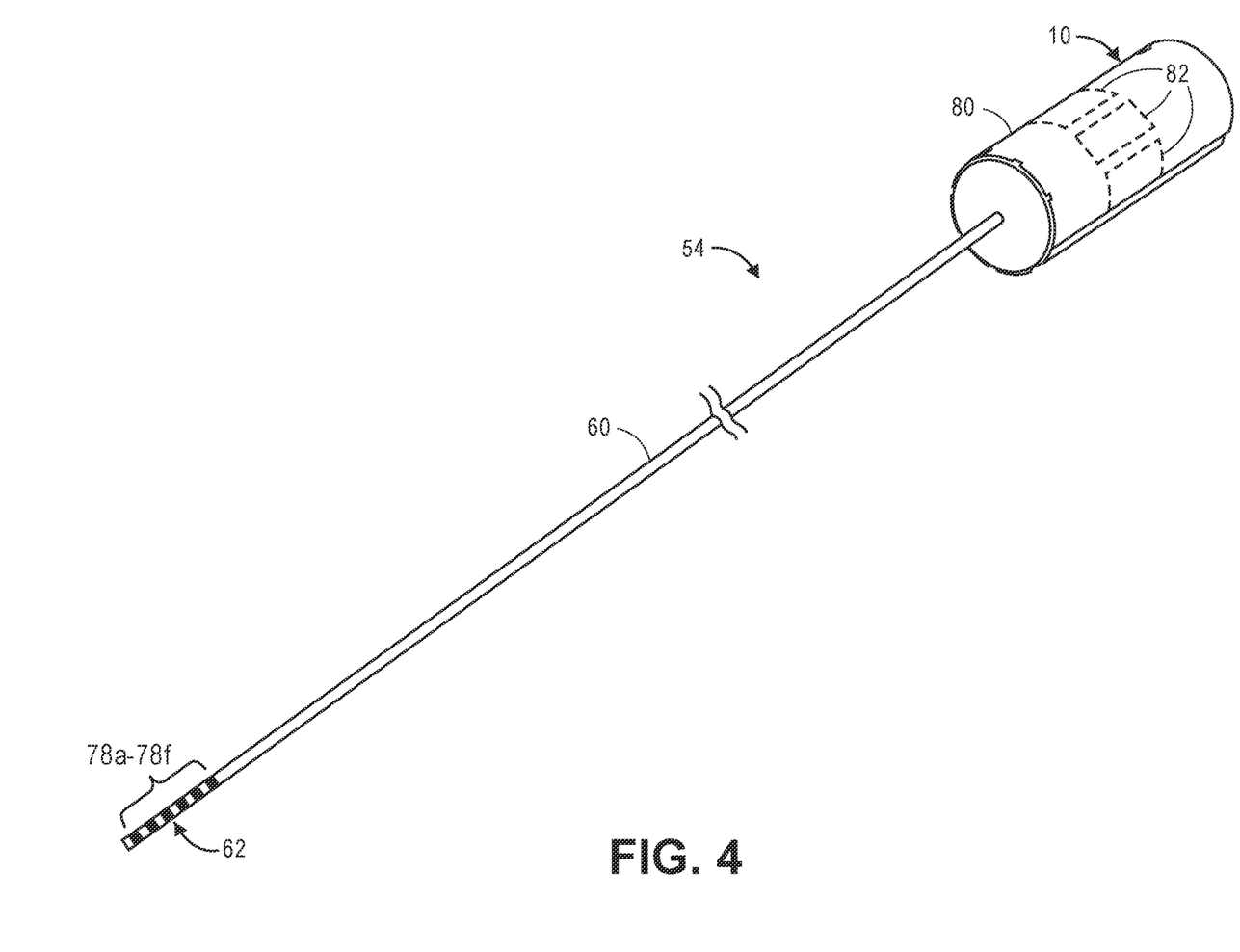
FIG. 4 is a perspective view of a lead electrode used in the stimulation system of FIG. 2.
Figure 5:
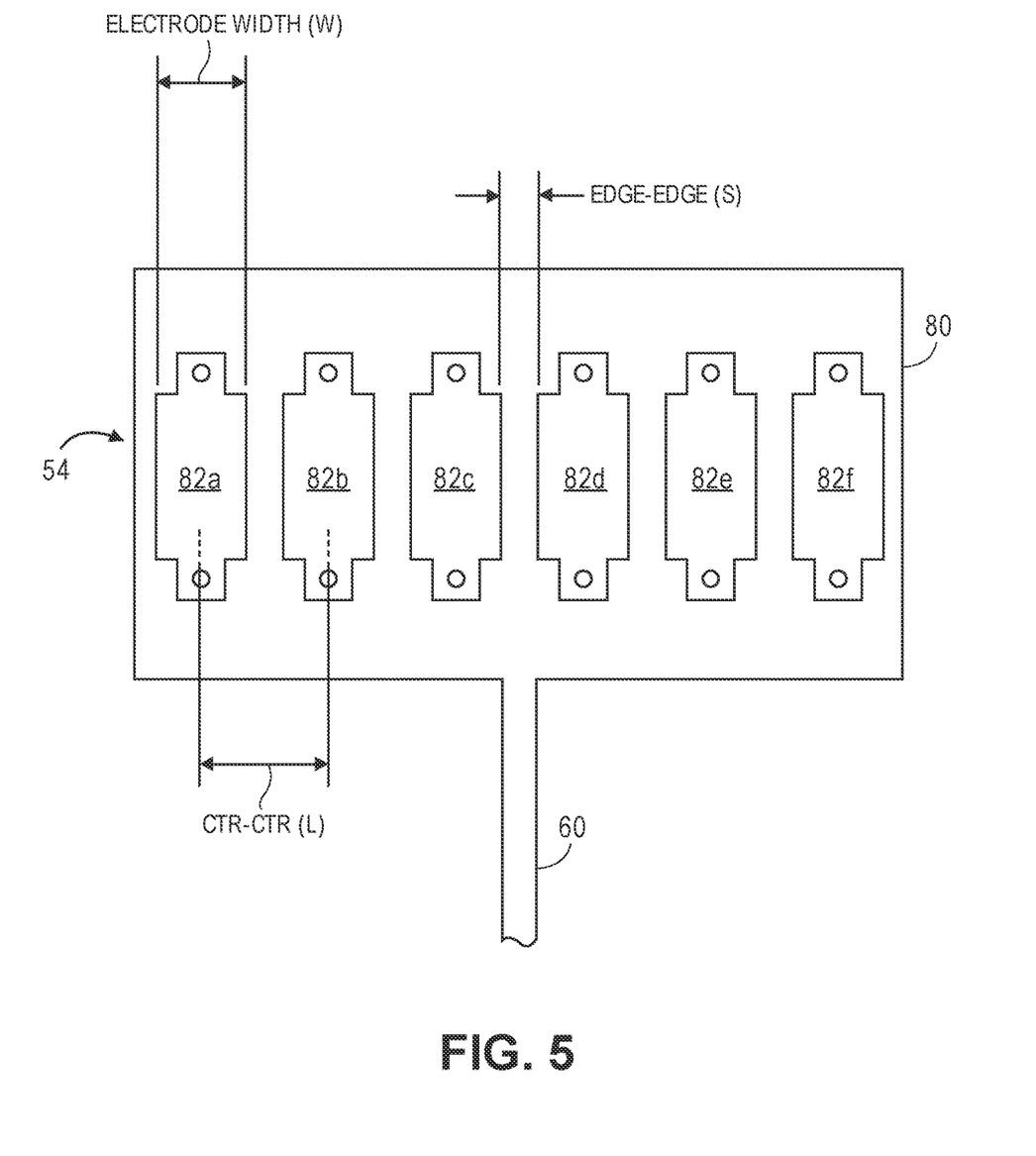
FIG. 5 is a plan view of a nerve cuff electrode of the lead electrode of FIG. 4, particularly shown in an unfurled state.
Figure 6:
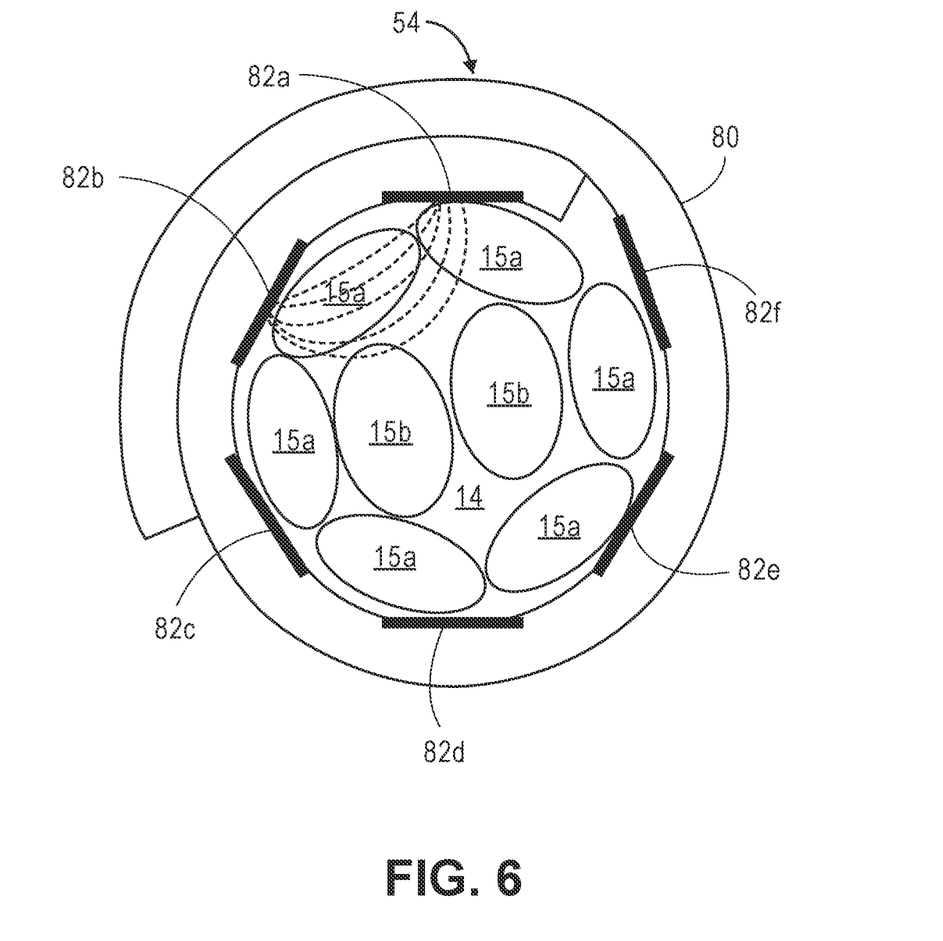
FIG. 6 is an end view of the nerve cuff electrode of FIG. 5, particularly shown in a furled state.

Referring further to FIGS. 4-6, the electrode lead 54 will now be described in further detail. The proximal lead connector 62 comprises a linear array of connector contacts 78a-78f (in this case, six) for connecting to the connector receptacle 64 of the IPG 52 when the proximal lead connector 62 is inserted into the connector receptacle 64. The nerve cuff electrode 10 comprises a nerve cuff body 80 that is capable of substantially or completely encircling the HGN trunk 14, and an array of electrode contacts 82a-82f (in this case, six) affixed to inside of the cuff body 80, such that when the cuff body 80 encircles the HGN trunk 14, the electrode contacts 82a-82f are in contact with the HGN trunk 14.

To facilitate selective activation of the fascicles of the HGN trunk 14 that innervate the protrusor muscles, the electrode contacts 82 are affixed to the cuff body 80 in a manner, such that when the cuff body 80 encircles the HGN trunk 14, the electrode contacts 82 are circumferentially disposed about the HGN trunk 14. In this case, the electrode contacts 82 span the cuff body 80 circumferentially around the HGN trunk 14.

Although in some embodiments, the nerve cuff electrode 10 may be operated in a monopolar stimulation mode, requiring that only one electrode contact 82 of the nerve cuff electrode 10 be activated at any given time, as will be described in further detail below, it is desirable that the nerve cuff electrode 10 be operated in a bipolar stimulation mode, requiring that at least two electrode contacts 82 of the nerve cuff electrode 10 be activated at any given time. Although the exemplary nerve cuff electrode 10 comprises six electrode contacts 82a-82f, other nerve cuff electrodes may have two to five electrode contacts 82 or more than six electrode contacts 82. The preferred range, however, of the numbers of electrode contacts 82 on any particular nerve cuff electrode is between three to eight electrode contacts 82, so as to surround the circumference of the HGN trunk 14, and provide a sufficient number of independent electrode channels from which to select and to recruit the protrusor muscles without recruiting the retractor muscles. The connector contacts 78a-78f are respectively and independently electrically coupled to the electrode contacts 82a-82f via electrical conductors (not shown), such that the electrode contacts 82a-82f may be independently activated in either monopolar stimulation mode or bipolar stimulation mode. In the monopolar stimulation mode, one or more of the electrode contacts 82a-82f will preferably be activated as cathode(s), whereas in the bipolar stimulation mode, one or more of the electrode contacts 82a-82f will be activated as cathode(s), and one or more other electrode contacts 82a-82f will be activated as anode(s).

The nerve cuff electrode 10 may be manufactured to be self-curling. The material used for the electrode substrate can be typical implantable electrode materials such as silicone, polyurethane or other materials, such as liquid crystal polymers. The material consistency of the formed cuff body 80 should be pliable enough to allow the clinician to unfold the cuff, as shown in FIG. 5, and placed around the HGN trunk 14 and to have the nerve cuff electrode 10 curl back around itself, as shown in FIG. 6. The substrate material of the nerve cuff body 80, therefore, should have a memory property to the extent that it will tend to return to its original curled shape. In one advantageous manufacturing process, the nerve cuff electrode 10, lead body 60, and proximal lead connector 62 may be constructed of a flexible circuit, as described in U.S. Patent Publication Nos. 2018/0117312 and 2018/0117313, and entitled "Nerve Cuff Electrodes Fabricated Using Over-Molded LCP Substrates," which are expressly incorporated by reference in their entirety.

The nerve cuff electrode 10, as shown, will also have some give, so that when the nerve swells during the inflammatory phase post-surgery, the inner lumen size of the nerve cuff electrode 10 can expand and accommodate to the nerve swelling. This capability of self-adjustment over time is important because once tissue has been dissected from around the nerve, there will be an inflammatory body response around the damaged tissue and also in response to the presence of foreign matter that may be introduced during the surgical implantation of the nerve cuff electrode 10. Indeed, the nerve cuff electrode 10, itself, is likely seen as a foreign matter contributing to inflammation. The inflammatory response may be ongoing over a period of months. During this period, the nerve, itself, may swell up and increase substantially in diameter, perhaps up to 50% more than before the surgery. Once past this inflammatory response, the nerve diameter may then decrease in size, closer to its original diameter. If the inner lumen size of the nerve cuff electrode 10 does not adjust in size to accommodate the increase in the nerve diameter, constriction of the target nerve can result in traumatic cell damage and nerve death. Further details describing various self-expanding nerve cuff electrodes are set forth in U.S. patent Publication No. 2018/0318577, entitled "Nerve Cuff Electrode Locking Mechanism," and U.S. Patent Publication No. 2018/0318578, "Self-Expanding Nerve Cuff Electrode" (now U.S. Pat. No. 10,981,000), which claim the benefit of priority to U.S. Provisional Patent Application Ser. No. 62/500,080, filed on May 2, 2017, entitled "Nerve Cuff Electrode Locking Mechanism," and U.S. Provisional Patent Application Ser. No. 62/500,091, filed on May 2, 2017, entitled "Self-Expanding Nerve Cuff Electrode," all of which are expressly incorporated herein by reference in their entirety.

As briefly discussed above, it is desirable to operate the nerve cuff electrode 10 in a bipolar mode in order to facilitate selective recruitment of the fascicles 15 in the HGN trunk 14. That is, monopolar stimulation results in a more diffuse electrical field that will tend to recruit most fascicles 15 in the HGN trunk 14, whereas bipolar stimulation results in a more specific and confined electrical field that will tend to recruit less non-targeted fascicles 15 in the HGN trunk 14. Thus, the fascicles 15 in the HGN trunk 14 that innervate the tongue protrusor muscles can be more selectively activated via bipolar stimulation. Because the electrode contacts 82 will circumferentially surround the HGN trunk 14, the electrical field generated by the nerve cuff electrode 10 in the bipolar stimulation mode can be selectively steered around the HGN trunk 14 to recruit the desired fascicles 15 within the HGN trunk 14. It is further noted that, because the fascicles 15 innervating the tongue protrusor muscles are peripherally located at the proximal position 20 to the HGN branches 18, it is desirable that adjacent electrode contacts 82 can be activated in the bipolar arrangement, such that the electrical field extends only peripherally into the HGN trunk 14. Thus, with reference to FIG. 6, it may be desirable to activate electrode contact pair 82a-82b, electrode contact pair 82b-82c, electrode contact pair 82c-82d, electrode contact combination 82d-82e, electrode contact combination 82e-82f, or electrode combination 82f-82a. As shown in FIG. 6, electrode combination 82a-82b are shown to be activated to create a confined bipolar electrical field therebetween that recruits one or more of the peripherally located fascicles 15a, as opposed to recruiting the centrally located fascicles 15b. Of course, any of the other electrode combinations can be operated in a bipolar manner to recruit other peripherally located fascicles 15a. The first one of the electrode contacts 82 in the combination can be a cathode, and the second one of the electrode contacts 82 in the combination can be an anode, or vice versa.

Notably, the strongest electrical field generated by the nerve cuff electrode 10 will be beneath an active electrode contact/cathode. Thus, in order to effectively employ bipolar stimulation, the nerve cuff electrode 10 may have the following design constraint: L≤2W, where W is the width of each electrode contact 82, and L is the center-to-center distance between two adjacent electrode contacts 82, as illustrated in FIG. 5. This constraint is based on the commercial needs in neuromodulation therapies to cover the most distance with spatial separations L and using the fewest number of electrode contacts 82. The width of the electrode contacts 82 will typically be based on the particular neural element that will be stimulated or the size of the cuff body 80, or a combination thereof, and will set the strength ranges of the electric fields generated by the nerve cuff electrode 10. As the center-to-center distance L exceeds the L≤2W design constraint, the electric field generated by a bipolar pair of electrode contacts 82 quickly starts to resemble a monopolar electric field as if there is a remote anode (unless there is a dramatic increase in the electric field amplitude). The ability of perform current steering between two or more adjacent electrode contacts 82 also weakens. In contrast, if adjacent electrode contacts 82 are too close or touching each other, there may be bleeding of electrical fields across the active contacts 82 at a higher amplitude, thereby creating a short that changes the ability to spatially select fascicles. Thus, it is important that the center-to-center distance L between adjacent electrode contacts 82 and the width W of the electrode contacts 82 be constrained.

However, because the size of the HGN 12 varies within the human population (e.g., between 2.5 mm and 4.00 mm), the effective distance between the electrode contacts 82a, 82f of a nerve cuff electrode 10 when wrapped around a HGN trunk 14 may vary with the size of the HGN trunk 14, thereby requiring nerve cuff electrodes to be made in different sizes.

Figure 7A:
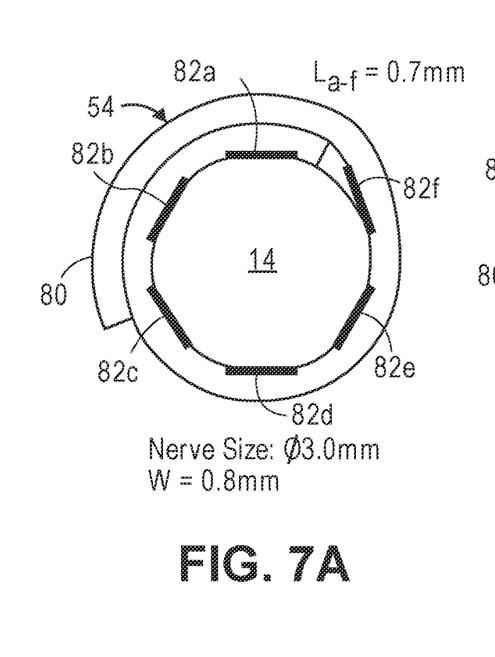
FIGS. 7a-7c are cross-sectional views of the nerve cuff electrode of FIGS. 5 and 6 wrapped around differently sized HGN trunks.
Figure 7B:
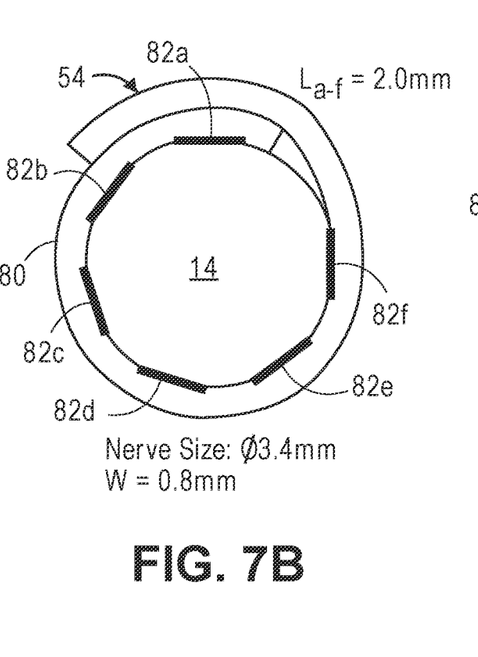
Figure 7C:
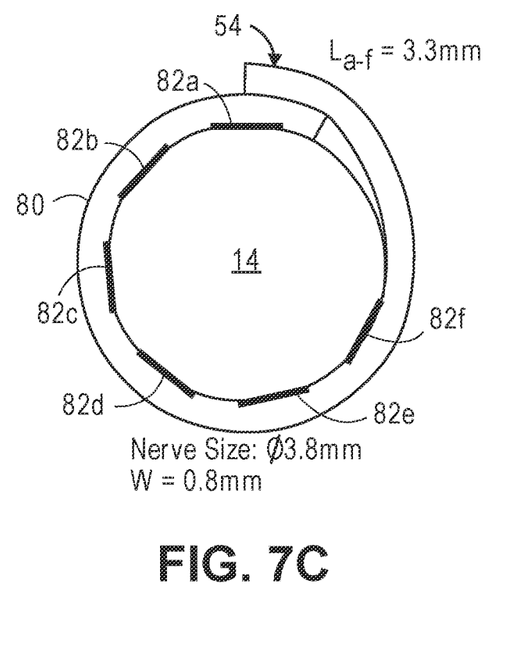

For example, as shown in FIGS. 7a-7c, the distance between the electrode contacts 82a, 82f (shown to have widths W of 0.8 mm) will increase as the diameter of the HGN trunk 14 increases from 3.0 mm to 3.8 mm. However, it is desirable that the distance between the electrode contacts 82a, 82f be maintained in accordance with the L≤2W design constraint to ensure that bipolar stimulation using the electrode contacts 82a, 82f is effective. As illustrated in FIG. 7a, the distance between electrode contacts 82a, 82f complies with the L≤2W design constraint. That is, the center-to-center distance $L_{a-f}$ between the electrode contacts 82a, 82f is shown to be 0.7 mm when the diameter of the HGN trunk 14 is 3.0 mm, thereby complying with the L≤2W design constraint (0.7 is less than (2×0.8)). However, as illustrated in FIGS. 7b and 7c, the distance between electrode contacts 82a, 82f violates the L≤2W design constraint, thereby causing the nerve cuff electrode 10 to have a "dead spot" between the electrode contacts 82a, 82f that would not be effective in bipolar stimulation. That is, the center-to-center distance $L_{a-f}$ between the electrode contacts 82a, 82f is shown to be 2.0 mm when the diameter of the HGN trunk 14 is 3.4 mm, thereby violating the L≤2W design constraint (2.0 is greater than (2×0.8)), and the center-to-center distance $L_{a-f}$ between the electrode contacts 82a, 82f is shown to be 3.3 mm when the diameter of the HGN trunk 14 is 3.8 mm, thereby violating the L≤2W design constraint (3.8 is greater than (2×0.8)).

In order to prevent the occurrence of a blind spot between the electrode contacts 82, and because there is variation in HGN nerve diameters, in the operating room, many different sizes of nerve cuff electrodes would need to be readily available to the surgeon. For example, in order to cover the range of HGN nerve sizes in the general population, at least five different sizes of nerve cuff electrodes would have to be fabricated and supplied to the surgeon in the operating room. Unused nerve cuff electrodes, opened during surgery, may need to be discarded, thereby increasing the cost of the surgical procedure. Furthermore, a surgeon will have to measure every HGN size to determine the right size of the nerve cuff electrode to be placed onto the HGN, which increases the time in the operating room. Measuring the HGN size requires very delicate work and can be quite subjective as well. Hence, the process is not only cumbersome and prone to error, but most importantly, poses the risk of damaging the HGN during the process to precisely measure the HGN.

Figure 8:
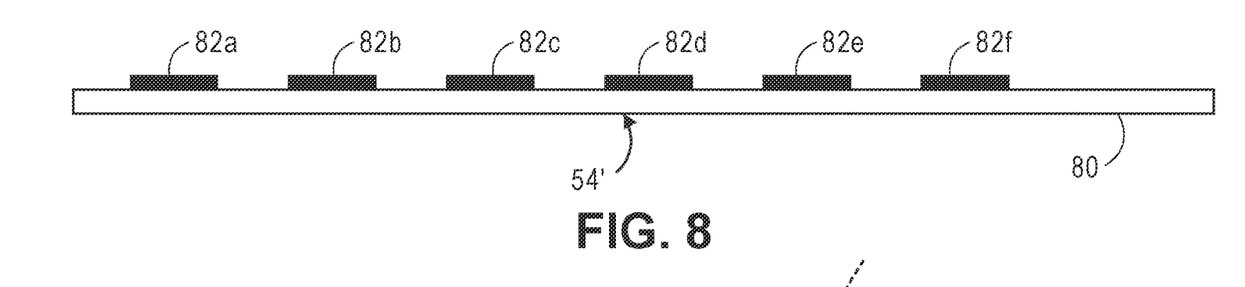
FIG. 8 is a profile view of an alternative nerve cuff electrode of the lead electrode of FIG. 4, particularly shown in an unfurled state.
Figure 9:
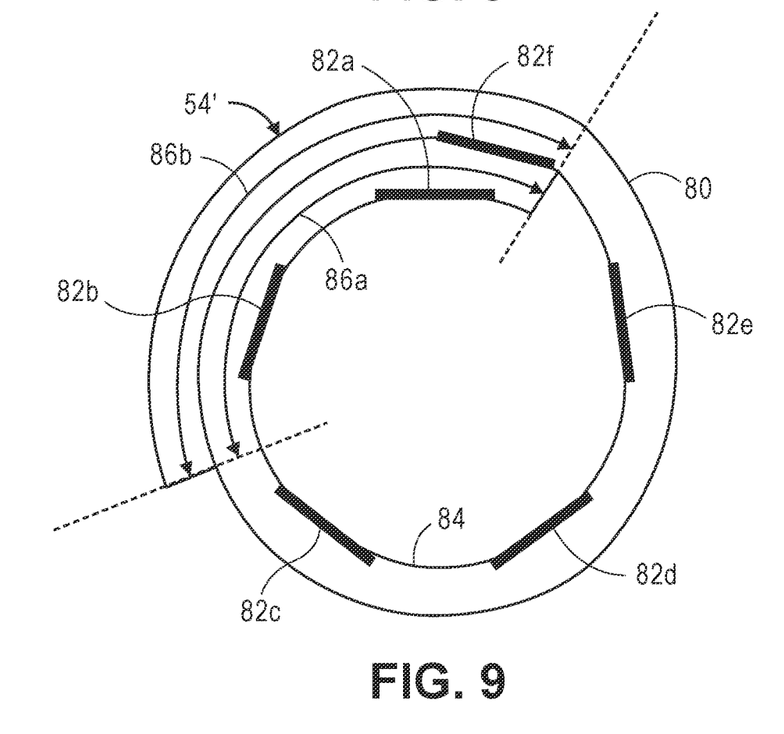
FIG. 9 is an end view of the nerve cuff electrode of FIG. 8, particularly shown in a furled state.

In accordance with the present inventions, one embodiment of a nerve cuff electrode 10' accommodates a large range of HGN sizes without creating blind spots, thereby eliminating the need to fabricate differently sized nerve cuff electrodes. In this embodiment, the array of electrode contacts 82 is disposed on the cuff body 80, and the cuff body 80 is pre-shaped to, in the absence of an external force, transition from an unfurled state (FIG. 8) to a furled state (FIG. 9). In one embodiment, the cuff body 80 will automatically transition from the unfurled state to the furled state in response to merely removing an external force from the cuff body 80. In another embodiment, the cuff body 80 is pre-shaped to curve in two orthogonal directions (along a lateral axis and a longitudinal axis), such that the cuff body 80 has a bi-stable structure. In this embodiment, an external force must be exerted on the cuff body 80 to transition it between the unfurled and furled state. Further details describing a bi-stable cuff body 80 are set forth in U.S Patent Publication Nos. 2018/0117312, entitled "Nerve Cuff Electrodes Fabricated Using Over-Molded LCP Substrates," and 2018/0117313, entitled "Nerve Cuff Electrodes Fabricated Using Over-Molded LCP," which have been expressly incorporated by reference.

In the unfurled state, all pairs of adjacent electrode contacts 82 (i.e., 82a-82b, 82b-82c, 82c-82d, 82d-82e, and 82e-82f) nominally comply with L≤2W design constraint. In the furled state, the cuff body 80 has an inner surface 84 capable of contacting the HGN trunk 14, as well as an overlapping inner cuff region 86a and outer cuff region 86b. Furthermore, when the cuff body 80 is in the furled state, the electrode contacts 82 are circumferentially disposed along the cuff body 80, such that at least one of the electrode contacts 82 is located on the inner surface 84 of the cuff body 80, and at least another one of the electrode contacts 82 is disposed between the overlapping inner and outer cuff regions 86a, 86b. Since the nominal distances between the respective pairs of adjacent electrode contacts 82a-82b, 82b-82c, 82c-82d, 82d-82e, and 82e-82f are fixed and therefore will not change, it is expected that these distances will comply with the L≤2W design constraint when the cuff body 80 is in the furled state, and will therefore, provide effective bipolar stimulation as long as the respective electrode contact pairs are in contact with the HGN trunk 14. However, as will be described in further detail below, the distance between the electrode contact 82a and the electrode contact 82f will vary in accordance with the diameter of the HGN trunk 14.

Although only one electrode contact, and in this case the electrode contact 82f, is shown as being disposed between the overlapping inner and outer cuff regions 86a, 86b in FIG. 9, more than one electrode contact 82 may be disposed between the overlapping inner and outer cuff regions 86a, 86b. The number of electrode contacts 82 that are disposed between the overlapping inner and outer cuff regions 86a, 86b when the cuff body 80 is in the furled state can be selected by selecting the number of electrode contacts 82 and/or the nominal center-to-center distances between adjacent electrode contacts 82. That is, the number of electrode contacts 82 that are disposed between the overlapping inner and outer cuff regions 86a, 86b will tend to increase as the number of electrode contacts 82 increases and/or the nominal center-to-center distance between adjacent electrode contacts 82 increases. In the example shown in FIGS. 8 and 9, the number of electrode contacts 82 relative to the embodiment shown in FIGS. 5 and 6 remains the same (i.e., six total), but the nominal center-to-center distance L between adjacent electrode contacts 82 have been increased, resulting in one electrode contact 82 being disposed between the overlapping inner and outer cuff regions 86a, 86b when the cuff body 80 is in the furled state. Of course, if the nominal center-to-center distance L between adjacent electrode contacts 82 is increased and/or the number of electrode contacts 82 is increased, additional electrode contacts 82 may be disposed between the overlapping inner and outer cuff regions 86a, 86b when the cuff body 80 is in the furled state.

Advantageously, the nerve cuff electrode 10' is capable of being used with differently sized HGN trunks 14 while still complying with the L≤2W design constraint for all pairs of adjacent electrode contacts 82 that are in contact with the HGN trunk 14. In particular, the extent that the cuff body 80 furls will adjust in accordance with the diameter of the HGN trunk 14, such that one of the set of electrode contacts 82 at the end of the array of electrode contacts 82 (in this case, either the electrode contact 82e or the electrode contact 82f) will be in contact with the HGN trunk 14 adjacent to the next electrode contact 70 adjacent to this electrode contact 70 (in this case, the electrode contact 82e or the electrode contact 70d) in compliance with the L≤2W design constraint.

Figure 10A:
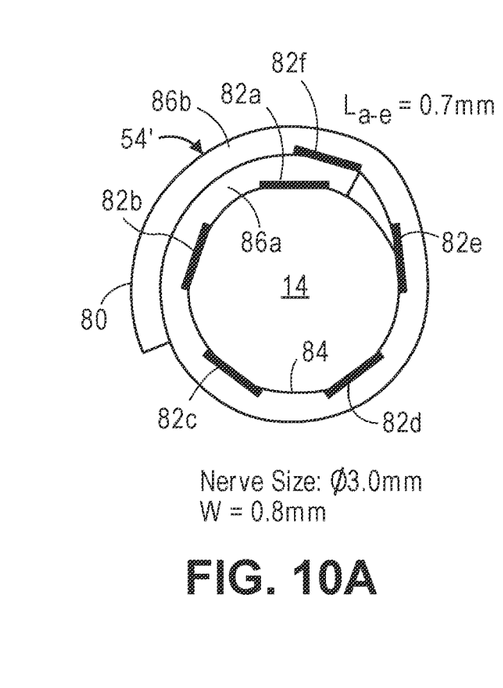
FIGS. 10a-10c are cross-sectional views of the nerve cuff electrode of FIGS. 8 and 9 wrapped around differently sized HGN trunks.
Figure 10B:
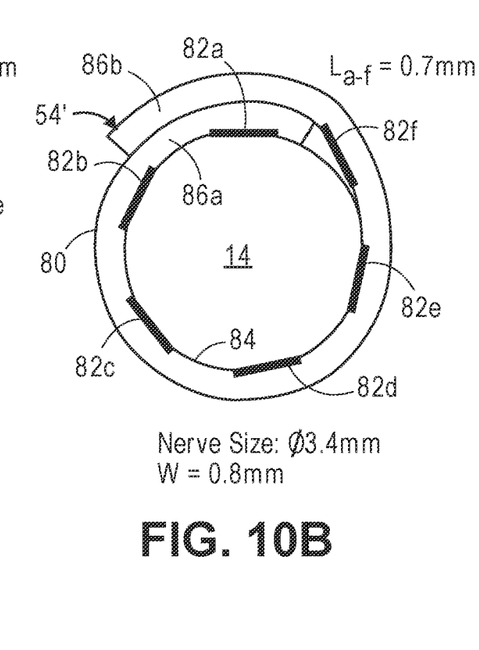
Figure 10C:
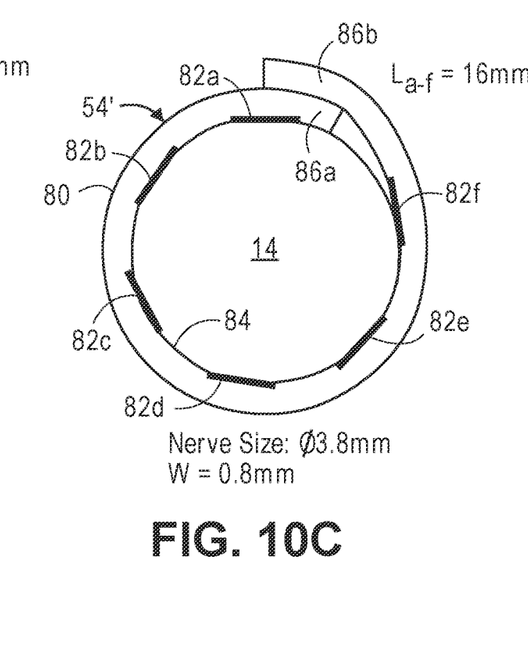

For example, as shown in FIGS. 10a-10c, for smaller diameter HGN trunks 14, the electrode contact 82f will be located between the overlapping inner and outer cuff regions 86a, 86b, but the next electrode contact 82e will be in contact with the HGN trunk 14 in a bipolar relationship with the electrode contact 82 in compliance with the L≤2W design constraint. However, as the diameter of the HGN trunk 14, the cuff body 80 will partially unfurl, causing the electrode contact 82f to be displaced from between the overlapping inner and outer cuff regions 86a, 86b to a position that is contact with the HGN trunk 14 in a bipolar relationship with the electrode contact 82 in compliance with the L≤2W design constraint.

Thus, as illustrated in FIG. 10a, the electrode contact 82f is between the overlapping inner and outer cuff regions 86a, 86b, such that it does not contact the HGN trunk 14. However, the electrode contact 82e is in contact with the HGN trunk 14 in a bipolar relationship with electrode contact 82a. The center-to-center distance $L_{a-e}$ between the electrode contacts 82, 82e is shown to be 0.7 mm when the diameter of the HGN trunk 14 is 3.0 mm, thereby complying with the L≤2W design constraint (0.7 is less than (2×0.8)). As illustrated in FIG. 10b, as the cuff body 80 partially unfurls due to the increased diameter of the HGN trunk 14, the electrode contact 82f is not between the overlapping inner and outer cuff regions 86a, 86b, but instead is in contact with the HGN trunk 14 in a bipolar relationship with electrode contact 82. The center-to-center distance $L_{a-f}$ between the electrode contacts 82a, 82f is shown to be 0.7 mm when the diameter of the HGN trunk 14 is 3.4 mm, thereby complying with the L≤2W design constraint (0.7 is less than (2×0.8)). As illustrated in FIG. 10c, as the cuff body 80 further partially unfurls due to the increased diameter of the HGN trunk 14, the center-to-center distance $L_{a-f}$ between the electrode contact 82f and the electrode contact 82a increases. However, the center-to-center distance L between the electrode contacts 82a, 82f is shown to be 1.6 mm when the diameter of the HGN trunk 14 is 3.8 mm, thereby complying with the L≤2W design constraint (1.6 is equal to (2×0.8)).

It should be appreciated that if it is desired to increase the range of diameter size of the HGN trunk 14 with which the nerve cuff electrode 10' used, such nerve cuff electrode 10' can be designed, such that more than one electrode contact 82 will be disposed between the overlapping inner and outer cuff regions 86a, 86b for the smallest designed diameter of the HGN trunk 14. For example, the number of electrode contacts 82 may be increased (e.g., from six to seven) or the cuff body 80 may be pre-shaped to have a smaller diameter in the absence of an external force.

Figure 11:
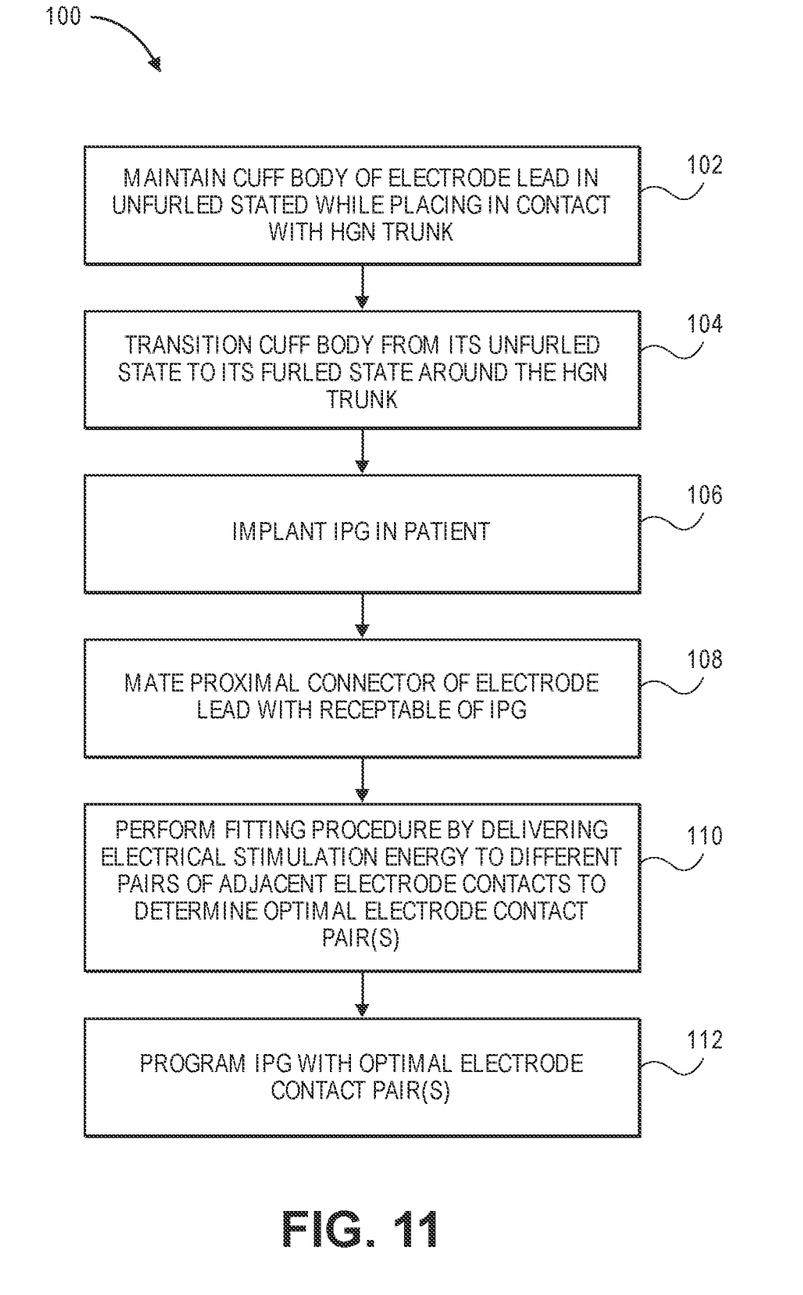
FIG. 11 is a flow diagram illustrating one method of implanting and fitting the stimulation system to a patient.

Having described the structure and function of the nerve cuff electrode 10', one method 100 of implanting the nerve cuff electrode 10' in a patient will now be described with reference to FIG. 11. First, the cuff body 80 is maintained in the unfurled state (FIG. 8) while placing the cuff body 80 in contact with the HGN trunk 14 (step 102). For example, the unfurled cuff body 80 may be placed underneath the HGN trunk 14. The cuff body 80 may be maintained in the unfurled state by, e.g., applying an external force to the cuff body 80 to prevent it from transitioning to the furled state, or if the cuff body 80 has a bi-stable structure, the cuff body 80 may be maintained in the unfurled state by not applying an external force to transition it to the furled state.

Next, the cuff body 80 is transitioned from the unfurled state into the furled state, such that the cuff body 80 wraps around the HGN trunk 14 (step 104). The cuff body 80 may be placed from the unfurled state into the furled state by, e.g., merely removing the external force from the cuff body 80, such that the cuff body 80 automatically transitions from the unfurled state to the furled state, or if the cuff body 80 has a bi-stable structure, an external force may be exerted on the cuff body 80 to transition it from the unfurled state to the furled state.

If the size of the HGN trunk 14 is relatively small, the cuff body 80 may wrap upon itself, as shown in FIG. 10a. In this case, there exists an inner surface 84 that contacts the HGN trunk 14 and an overlapping inner cuff region 86a and an outer cuff region 86b, and the electrode contacts 82 that are on the inner surface 84 of the cuff body 80 is contact with the HGN trunk 14, and at least another of the electrode contacts 82 is between the inner and outer overlapping regions 86a, 86b of the cuff body 80 without contacting the HGN trunk 14. If the size of the HGN trunk 14 is relatively large, the cuff body 80 may be prevented from wrapping upon itself, as shown in FIGS. 10b and 10c. In this case, all electrode contacts 82 will be in contact with the HGN trunk 14. In all cases, the center-to-center spacing L of each respective pair of adjacent electrode contacts 82 is equal to or less than twice the width W of each electrode contact 82 of the respective pair of adjacent electrode contacts 82.

Next, the IPG 52 is implanted within the patient (step 106), and the proximal lead connector 62 is mated with the receptacle 64 of the IPG 52 (step 108). Next, electrical stimulation energy is delivered to a pair of adjacent ones of the electrode contacts 82 to stimulate the HGN trunk 14 in a bipolar mode, and preferably, the fascicles of the HGN trunk 14 innervating the tongue protrusor muscles (step 110). Step 110 can be repeated for different pair of electrode contacts 82 to find the optimal electrode contact pairs in a fitting procedure. Lastly, the IPG 52 is programmed with the optimal electrode contact pair(s) using the clinician programmer 56 (step 112).

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method of stimulating a nerve of a patient to treat an ailment, the nerve having a plurality of peripherally located fascicles and at least one centrally located fascicle, the method comprising:

circumferentially disposing a plurality of axially aligned electrode contacts around the nerve, such that each of all available pairs of immediately adjacent ones of the plurality of electrode contacts has a center-to-center circumferential spacing that is equal to or less than twice the circumferential width of an electrode contact of the respective pair of immediately adjacent electrode contacts; and delivering an electrical pulse train between a pair of immediately adjacent ones of the plurality of electrode contacts, thereby creating a confined bipolar electrical field that recruits one or more of the peripherally located fascicles to treat the ailment, while not recruiting the at least one centrally located fascicle.

2. The method of claim 1, wherein the nerve has a diameter in the range of 2.5 mm to 4.0 mm.

3. The method of claim 1, wherein the plurality of electrode contacts comprises at least three electrode contacts.

4. The method of claim 1, wherein the plurality of electrode contracts comprises at least six electrode contacts.

5. The method of claim 1, wherein the peripherally located fascicles innervate tongue protrusor muscles of the patient.

6. The method of claim 5, wherein the nerve is a hypoglossal nerve (HGN) trunk.

7. The method of claim 6, wherein the pair of immediately adjacent ones of plurality of electrode contacts is located on the HGN trunk proximal to a medial branch of the HGN trunk.

8. The method of claim 6, wherein the ailment is obstructive sleep apnea (OSA).

9. The method of claim 1, further comprising delivering another electrical pulse train between another pair of immediately adjacent ones of the plurality of electrode contacts, thereby creating another confined bipolar electrical field that recruits a different one or more of the peripherally located fascicles to treat the ailment, while not recruiting the at least one centrally located fascicle.

10. The method of claim 1, wherein none of the at least one centrally located fascicle is recruited by the electrical pulse train delivered to the pair of immediately adjacent electrode contacts.

11. The method of claim 1, further comprising repeating the electrical pulse train delivery step for different pairs of immediately adjacent ones of the plurality of electrode contacts until all peripherally located fascicles of the nerve have been recruited.

* * * * *